(12) United States Patent
Crews-Ketterling et al.

(10) Patent No.: US 12,224,056 B1
(45) Date of Patent: Feb. 11, 2025

(54) SYSTEM AND METHOD FOR SELF-REGULATING BRAIN PATTERNS

(71) Applicants: Debra Crews-Ketterling, Mesa, AZ (US); Lorre Anderson, Chandler, AZ (US); Susannah Wearne, Phoenix, AZ (US)

(72) Inventors: Debra Crews-Ketterling, Mesa, AZ (US); Lorre Anderson, Chandler, AZ (US); Susannah Wearne, Phoenix, AZ (US)

( * ) Notice: Subject to any disclaimer, the term of this patent is extended or adjusted under 35 U.S.C. 154(b) by 162 days.

(21) Appl. No.: 18/160,746

(22) Filed: Jan. 27, 2023

(51) Int. Cl.
  *G16H 20/70* (2018.01)
  *G16H 40/63* (2018.01)

(52) U.S. Cl.
  CPC .............. *G16H 20/70* (2018.01); *G16H 40/63* (2018.01)

(58) Field of Classification Search
  CPC ..................................................... G16H 20/70
  USPC ............................................................ 705/2
  See application file for complete search history.

(56) References Cited

U.S. PATENT DOCUMENTS

| | | | |
|---|---|---|---|
| 5,219,322 A | 6/1993 | Weathers | |
| 8,990,054 B1 | 3/2015 | Ketterling et al. | |
| 2018/0169411 A1* | 6/2018 | Goodall | A61N 1/37247 |
| 2021/0405276 A1* | 12/2021 | Brick | H01L 25/0753 |

FOREIGN PATENT DOCUMENTS

| WO | WO-2022056002 A1 * | 3/2022 | ............. A61B 5/378 |
|---|---|---|---|

OTHER PUBLICATIONS

Hecht, David et all; Sensory dominance in combinations of audio, visual and haptic stimuli; Experimental Brain Research 193.2: 307-14. Springer Nature B.V. (Feb. 2009) (Year: 2009).*
Webpage printout: https://www.emdr.com/what-is-emdr/ from the EMDR institute, Inc. "What is EMDR?" Eye Movement Desensitization and Reprocessing, copyright date 2020 EMDR Institute, Inc.
Webpage printout: https://www.psychiatrictimes.com/view/accelerated-resolution-therapy-ptsd, an article from Psychiatric Times, vol. 35, Issue 8, titled "Acceleratd Resolution Therapy for PTSD" dated Aug. 30, 2018 by Wendi Waits, MD.

* cited by examiner

*Primary Examiner* — Hiep V Nguyen
(74) *Attorney, Agent, or Firm* — Tuggle Duggins P.A.; Blake P. Hurt; Reinier R. Smit (57) ABSTRACT

A system and method for individual administration of a brain programming session including providing a device to provide visual, haptic, and audio stimuli to an individual at relevant times during the brain programming session. The system and method further include providing a list of directives configured to be executed by the individual during the brain programming session. The list of directives may reduce the individual's emotional responses to past events and conditions or to program mindsets and emotions for future performances and events. While executing the list of directives, the individual will experience visual, haptic, and audio stimuli provided by the device. Completion or partial completion of a list of directives results in brain activity being more balanced across brain regions when experiencing past events or conditions that yield an emotional response or when experiencing future performances and events for which the individual has programmed mindsets and emotions.

18 Claims, 8 Drawing Sheets
(3 of 8 Drawing Sheet(s) Filed in Color)

| Synergy/Calm Low | Synergy/Calm Moderate | Synergy/Calm High | Synergy/Calm Exceptional |
|---|---|---|---|
| 59% and below | 60% - 69% | 70% - 79% | 80% and above |

SYSTEM AND METHOD FOR SELF-REGULATING BRAIN PATTERNS

This application incorporates by reference in its entirety U.S. Pat. No. 8,990,054 issued 24 Mar. 2015 entitled "System and Method for Determining and Training a Peak Performance State" with inventors Debra C. Ketterling and Kanav Kahol.

FIELD OF THE INVENTION

The disclosure herein pertains to regulation of habits, and specifically to system and method for self-regulating brain patterns.

DESCRIPTION OF THE PRIOR ART AND OBJECTIVES OF THE INVENTION

Severe emotional trauma can require a significant amount of time to heal. Individuals negatively impacted from horrific events often struggle to process their own trauma, leading to delayed and potentially ineffective healing. Those suffering from severe emotional pain may have difficulty eliminating neurological barriers to their own recovery. Their responses to these traumatic events may become dysfunctional. Accordingly, therapies have been developed with the goal of removing these neurological barriers and accelerating the healing process.

Cognitive Behavior therapy addresses the event(s) that cause the trauma and primarily use the prefrontal cortex of the brain to talk through the event. Eye Movement Desensitization and Reprocessing (EMDR) is a therapy session that was originally designed to alleviate the distress associated with traumatic memories done under the supervision and guide of a licensed therapist. (*Eye Movement Desensitization and Reprocessing: Basic Principles, Protocols and Procedures* (2nd edition). New York: Guilford Press) EMDR therapy facilitates the accessing and processing of traumatic memories and other adverse life experiences to bring these to an adaptive resolution. After a successful session with EMDR therapy, affective distress is relieved, negative beliefs are reformulated, and physiological arousal is reduced. EMDR therapy involves the individual attending to emotionally disturbing material in brief, sequential sessions while simultaneously focusing on an external stimulus. This process addresses the memories associated with the trauma and is focused on altering the storage of the memories in the hippocampus, the neocortex, and the amygdala. Forming habits that do not serve the individual are yet another phenomena that affect dealing with trauma. These habits are stored primarily in the basal ganglia, the oldest part of the brain. Breaking habits and making new habits is an important skill for self-regulation. By repatterning the brain, it is likely that all three phenomena (Cognitive Behavior therapy, EMDR, and habit formation) are influenced and all these areas of the brain are being repatterned. While these current therapies focus primarily on healing the past, this patent application focuses on the reprogramming the past and more importantly, creating new patterns for the future. The goal is health and success.

EMDR is the technique that is closest in structure to the current patent application. In EMDR, typically, therapist-directed lateral eye movements are used as external stimulus but a variety of other stimuli including hand-tapping and audio stimulation may be used (Shapiro (1991), Eye movement desensitization & reprocessing procedure: From EMD to EMD/R-a new session model for anxiety and related traumata). Dr. Francine Shapiro (Shapiro, F. (1995). Eye Movement Desensitization and Reprocessing: Basic Principles, Protocols and Procedures (1st edition). New York: Guilford Press; See Shapiro, F., (2001). Eye Movement Desensitization and Reprocessing: Basic Principles, Protocols and Procedures (2nd edition). New York: Guilford Press) It has been hypothesized that EMDR therapy allows the individual to access the traumatic memory network, so that information processing is enhanced, with new associations forged between the traumatic memory and more adaptive memories or information. These new associations are thought to result in a complete information processing, new learning, elimination of emotional distress, and development of cognitive insights. EMDR therapy employs a three-pronged procedure. First, the past events that have laid the groundwork for disfunction are processed, forging new associative links with adaptive information. Second, the current circumstances that elicit distress are targeted, and internal and external triggers are desensitized. Third, and finally, imaginal templates of future events are incorporated, to assist the client in acquiring the skills needed for adaptive functioning. Repeated studies have shown that EMDR therapy individuals experience the benefits of brain programming at an accelerated pace compared to other methods of therapy. One study found that 100% of the single-trauma victims and 77% of multiple trauma victims were no longer diagnosed with post-traumatic stress disorder (PTSD) after only six (6) fifty (50) minute sessions, and another study found that 77% of combat veterans were free of PTSD after twelve (12) sessions. Generally, however, EMDR therapy can take between five to fifteen (5-15) sessions or more.

Accelerated Resolution Therapy (ART) is an emerging, efficient therapy for PTSD that is derived from EMDR therapy. Much like EMDR therapy, ART employs analogous methods to achieve potentially similar goals, namely to "fulfill the brain's requirements for allowing new learning to rewrite and erase an old, unwanted learning—and not merely suppress and compete against the old learning". The ART procedure aims to extinguish an individual's fear response while unwiring distressing emotion from factual memories of the events that created them. To those ends, ART uses external stimulus much like EMDR therapy, namely eye movements. After having an introduction to the procedure, an individual can complete an ART session in about fifty to sixty (50-60) minutes with 3.7±1.1 sessions often needed to yield results. One study involving combat veterans and active-duty service members found that ART demonstrated a 61% response rate and a 94% competition rate. The low number of sessions needed is particularly advantageous because 83% of individuals who drop out of therapy that are undergoing traditional evidence-based therapies for PTSD do so before their fifth session. Clinical trials of ART have yielded promising results; however, as a consequence of ART's relatively recent development, the overall effectiveness of the procedure still has yet to be confirmed with sufficient testing. While ART is derived from EMDR therapy, it diverges from EMDR in some important ways. First, EMDR uses a variable number of eye movements, while ART uses a fixed number. Second, EMDR uses free association, while ART therapies are directed. Third, EMDR pays attention to content, whereas ART therapists focus on visual imagery and emotion sensations. Fourth, EMDR is content-oriented, whereas ART is procedure-oriented. Indeed, ART and EMDR diverge in numerous ways, but the same underlying concept and goals remain.

Both ART and EMDR, while effective, have a major shortcoming: they both require the presence of a trained brain programming professional, such as a psychiatrist, therapist or other trained individual, for each brain programming session. This shortcoming poses significant disadvantages such as requiring travel time by either the individual or the trained professional to conduct a brain programming session, financially burdening individuals with the expense of retaining a trained professional to administer the session, limiting individuals to receiving sessions only during the business hours of the trained professional, and delaying certain individual's recovery that have the capacity to receive sessions at a faster rate than other individuals.

Thus, in view of the problems and disadvantages associated with prior art therapies and systems, the present disclosure was conceived and one of its objectives is to provide a system and method for individual administration of a brain programming session that may be completed in about ten minutes.

It is another objective of the present disclosure to provide a system and method for individual administration of a brain programming session that includes a list of directives configured so that executing the list of directives, either partially or completely, and either one time or multiple times, reduces the emotional responses to past events, programs future events and patterns, and conditions and balances brain activity across regions of the brain.

It is still another objective of the present disclosure to provide a system and method for self-administration of a brain programming session that includes a list of directives configured so that executing the list of directives, either partially or completely, and either one time or multiple times, programs mindsets and emotions for future performances and events and balances brain activity across regions of the brain.

It is yet another objective of the present disclosure to provide a system and method for individual administration of a brain programming session that includes a list of directives configured so that executing the list of directives, either partially or completely, and either one time or multiple times, breaks habits and forms new habits and balances brain activity across regions of the brain.

It is a still yet another objective of the present disclosure to provide a system and method for individual administration of a brain programming session that may be administered independent of an instructor, counselor, psychologist, or any other additional person.

It is a further objective of the present disclosure to provide a system and method for individual administration of a brain programming session that provides a visual focus point that oscillates from left to right and back from right to left, but preferably from one lateral extreme of the individual's vision to the other lateral extreme of the individual's vision without moving the head.

It is still a further objective of the present disclosure to provide a system and method for individual administration of a brain programming session that includes providing a device configured to provide visual, haptic, and audio stimuli to the individual at predetermined times during the brain programming sessions.

It is yet a further objective of the present disclosure to provide a system and method for individual administration of a brain programming session that provides haptic and audio stimuli to the left side of the individual's body when the visual focus point changes direction from left to right and provides haptic and audio stimuli to the right side of the individual's body when the visual focus point changes direction from right to left.

It is still yet a further objective of the present disclosure to provide a system for self-guided, individual administration of a brain programming session that is configured to be easily transportable by the individual from one location to another.

Various other objectives and advantages of the present disclosure will become apparent to those skilled in the art as a more detailed description is set forth below.

SUMMARY OF THE INVENTION

The aforesaid and other objectives are realized by providing a system and method for individual administration of a brain programming session including providing a self-administration brain programming system that is configured to provide visual, haptic, and audio stimuli; providing a list of directives configured to balance brain activity across regions of the brain and configured to reduce emotional responses to past events and conditions, program mindsets and emotions for future performance and events, and/or break habits and make new habits; the list of directives may include activating the self-administration brain programming system at the beginning of the brain programming session, asking the individual to observe the visual stimuli while mentally or verbally engaging with a directive, and deactivating the self-administration brain programming system at the end of the session. In the preferred application, the system and method for individual administration of a brain programming session may be re-used multiple times by an individual until negative feelings and emotions about a past event or future event have been resolved and new brain patterns have been created.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENT AND OPERATION OF THE INVENTION

Various exemplary embodiments of the present disclosure are described below. Use of the term "exemplary" means illustrative or by way of example only, and any reference herein to "the disclosure" is not intended to restrict or limit the disclosure to exact features or step of any one or more of the exemplary embodiments disclosed in the present specification. References to "exemplary embodiment", "one embodiment", "an embodiment", "various embodiments", and the like may indicate that the embodiment(s) of the disclosure so described may include a particular feature, structure, or characteristic, but not every embodiment necessarily incudes the particular feature, structure, or characteristic. Further, repeated use of the phrase "in one embodiment", "in an exemplary embodiment", or "in an alternative embodiment" do not necessarily refer to the same embodiment, although they may.

It is also noted that terms like "preferably", "commonly", and "typically" are not utilized herein to limit the scope of the disclosure or to imply that certain features are critical, essential, or even important to the structure or function of the disclosure. Rather, these terms are merely intended to highlight alternative or additional features that may or may not be utilized in a particular embodiment of the present disclosure.

The present disclosure is described more fully hereinafter with reference to the accompanying figures, in which one or more exemplary embodiments of the disclosure are shown. Like numbers used herein refer to like elements throughout. The disclosure may, however, be embodied in many different forms and should not be construed as limited to the embodiments set forth herein; rather, these embodiments are provided so that this disclosure will be operative, enabling, and complete. Accordingly, the particular arrangements disclosed are meant to be illustrative only and not limited as to the scope of the disclosure, and any and all equivalents thereof. Moreover, many embodiments such as adaptations, variations, modifications, and equivalent arrangements will be implicitly disclosed by the embodiments described herein and fall within the scope of the instant disclosure.

Although specific terms are employed herein, they are used in a generic and descriptive sense only and not for the purposes of limitation. Unless otherwise expressly defined herein, such terms are intended to be given their broad, ordinary, and customary meaning not inconsistent with that applicable in the relevant industry and without restriction to any specific embodiment hereinafter described. As used herein, the article "a" is intended to include one or more items. Where only one item is intended, the terms "one and only one", "single", or similar language is used. When used herein to join a list of items, the term "or" denotes at least one of the items but does not exclude a plurality of items of the list.

For exemplary methods or processes of the disclosure, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present disclosure.

Additionally, any references to advantages, benefits, unexpected results, or operability of the present disclosure are not intended as an affirmation that the disclosure has previously been reduced to practice or that any testing has been performed. Likewise, unless stated otherwise, use of verbs in the past tense (present perfect or preterit) is not intended to indicate or imply that the disclosure has previously been reduced to practice or that any testing has been performed.

Figure 1:
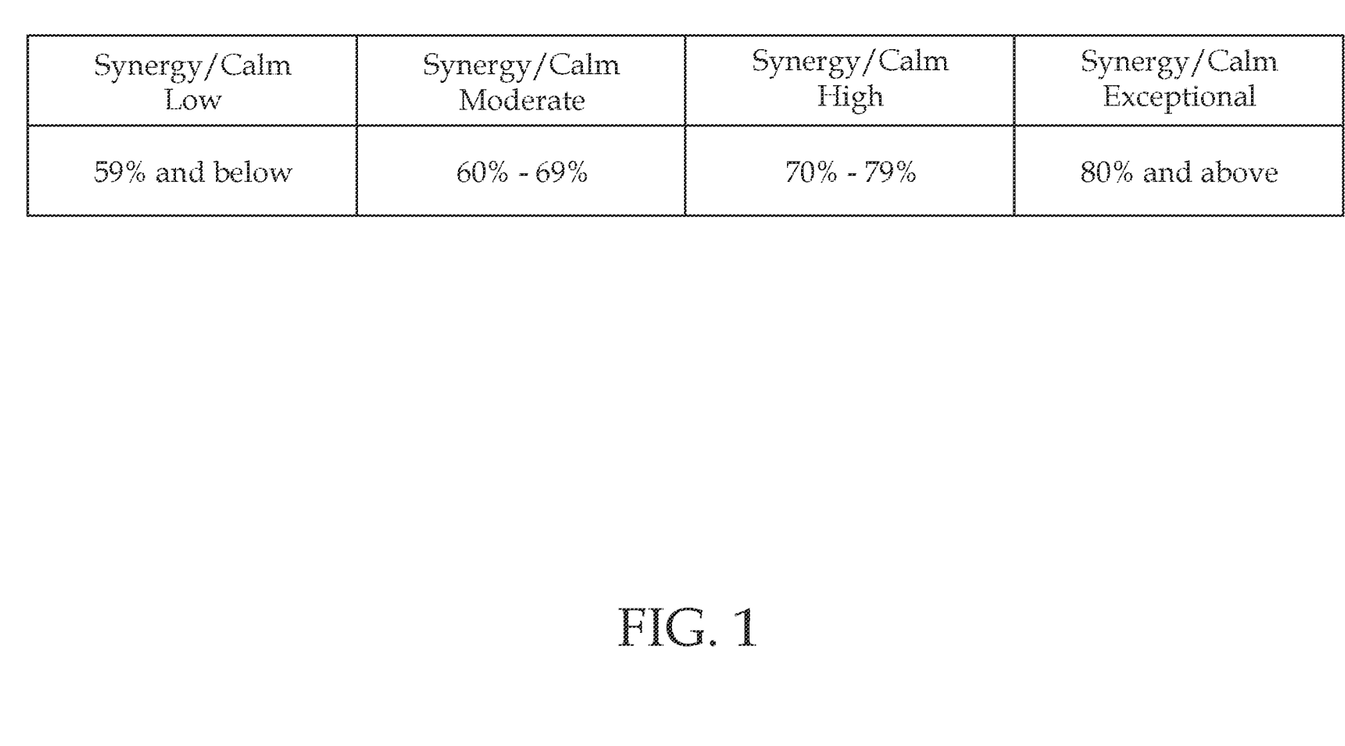
FIG. 1 shows a table displaying ranges for low, moderate, high, and exceptional synergy states of a brain.

As used herein, "synergy", the interaction or cooperation of two or more parts to produce a combined effect greater than the sum of their separate parts, is defined as how close the human brain is to a homeostatic state, i.e., the tendency toward a relatively stable equilibrium between interdependent elements, especially as maintained by physiological processes, where perfect synergy is equivalent to homeostasis. As understood the brain comprises right and left hemispheres, each having different sections within and joined by numerous fibers which transmit messages or electrical signals, between the sections and from one hemisphere to the other such that each respective hemisphere while controlling the opposite side of the body works together to achieve balance and synergy. Further each respective hemisphere while working together processes information differently, for example the senses: sight, sound, touch, taste, smell, any one of these or combination can evoke mental images or feelings whether positive or negative to be retained as memories and/or triggers ultimately affecting the mental and emotional state of a person. Any one of these can trigger different responses within parts of the brain which can be seen by the electrical signals sent between the sections and from one hemisphere to the other. The levels of this electrical activity in the brain may be measured and observed with electroencephalography which measures and records the activity in different parts of the brain for visual tracing or mapping of the affected areas and the balance between hemispheres. In addition, the brain electrical activity is broken into frequency bands to interpret different types of processing. There are 5 frequency bands that each infer processing states. Delta is sleep, theta is a meditative state, alpha is a learning state, beta processes information and gamma is the harmonizing frequency. Synergy, as we measure it, looks at location and frequencies (theta, alpha, beta and beta2). High electrical activity levels in one hemisphere or one quadrant (hereinafter collectively referred to as "regions"), or in one frequency band compared to the other regions of the brain or other frequency bands is indicative that the brain is in an unbalanced state, and thus a low synergy state. A brain is in a more balanced or high synergy state (see FIG. 1) when electrical activity is more evenly distributed across the regions of the brain and the 4 frequency bands, specifically when the brain is at least 70% balanced across the regions and frequency bands. When in a high synergy state, the brain may more easily form connections necessary to heal from a traumatic event. By comparison, a brain in a low synergy state (see FIG. 1) may be in a flight or fight response or otherwise agitated, rendering it unable to make the connections necessary to heal from a past, mentally traumatic event. Specifically, a brain is in a low synergy state when it is less than 59% balanced across the regions. Individuals who have experienced a mentally traumatic event may enter a state of low synergy whenever they recall the traumatic event, thereby preventing the individual from mentally recovering from the event. This re-entry into a low synergy state upon recalling a traumatic event is a "mental barrier" that the system and method detailed in the present disclosure seek to eliminate.

As used herein, "calm" is a measure of how much electrical activity is present in four locations of the brain at four different frequencies. Calm is preferably when a person is in a relaxed, tranquil state and not showing or feeling nervousness, fear, frustration, anger, or other strong, potentially negative emotions. Calm is high when the electrical activity in the brain is low. Generally low electrical values across areas of the brain translate to a high value for calm.

Figure 2:
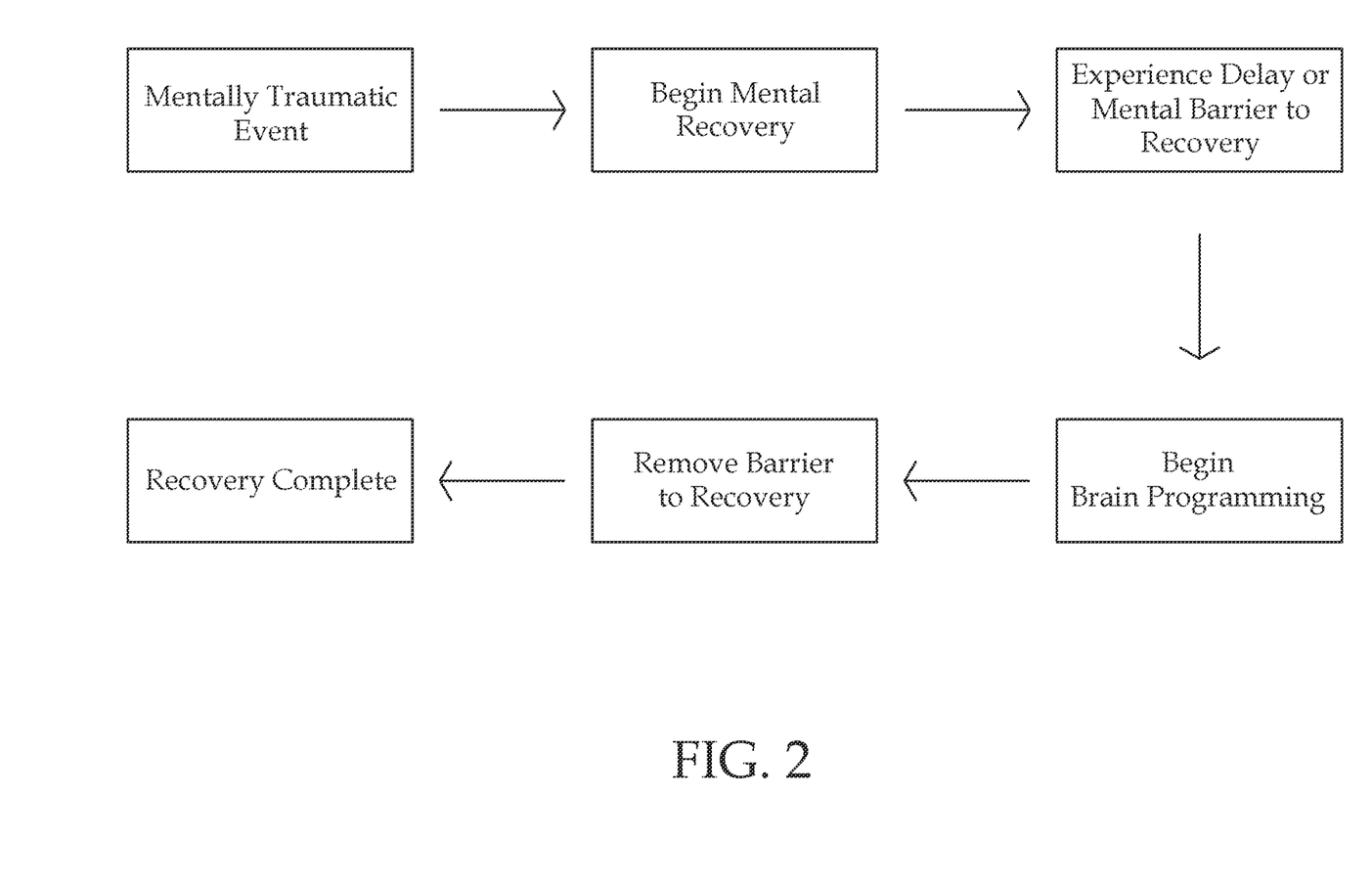
FIG. 2 pictures a flow chart of the series of events that may give rise to an individual needing brain programming to recover from a past mentally traumatic event.
Figure 3:
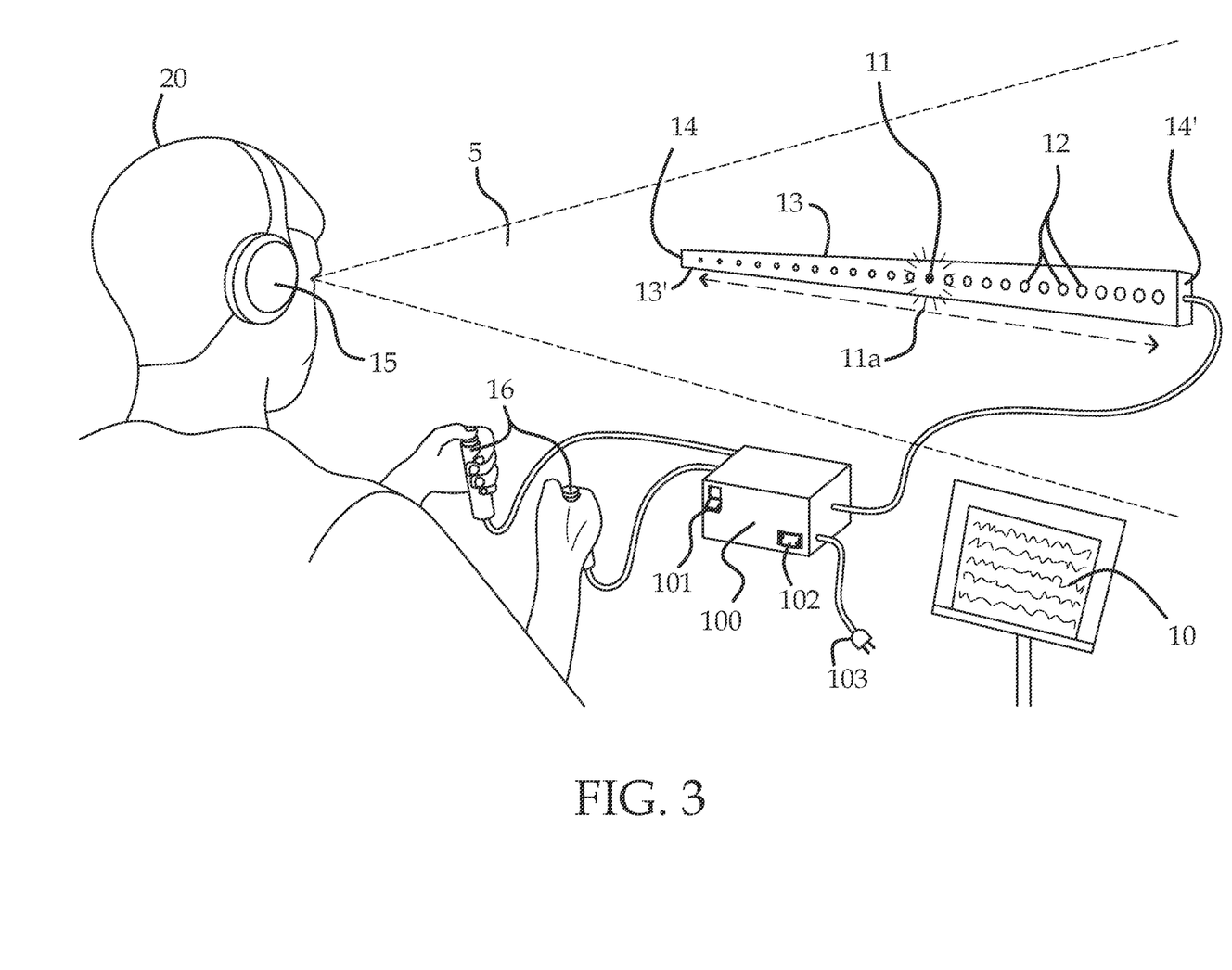
FIG. 3 shows an individual self-administering a brain programming session incorporating a list of directives and a device configured to provide visual, audio, and haptic stimuli to the individual during the brain programming session.

For a better understanding of the present disclosure and its operation, FIG. 2 details an exemplary series of events that may lead an individual to needing psychological help through brain programming. First, the individual experiences an emotionally disturbing or traumatic event. Next, after being removed from the traumatic event, the individual begins the recovery process wherein the individual's mind starts recovering from the trauma. Then, during the recovery process the individual is unable to resolve a mental barrier that prevents or delays the individual's full mental recovery. Next, to remove the mental barrier, the individual may begin a session or series of sessions of a brain programming session. Further, the brain programming session or series of sessions facilitates the removal of the mental barrier. Finally, the individual is then able to continue the recovery process, ideally resulting in a full mental recovery. The process listed in FIG. 3 is a preferred example, any one brain programming session may be effective or more effective for one individual but not another individual. Typically, determining which brain programming session is the best for a particular individual is an iterative process that relies on one trained in the art to direct, but shortly an individual may start on one session experience with little to no success and be transferred to another session and so on until the mental barrier has been removed. Once the mental barrier has been removed and a session plan created for the individual's recovery, self-guidance would be beneficial for an individual who feels comfortable and confident in the process to self-administer a brain programming session.

Figure 4:
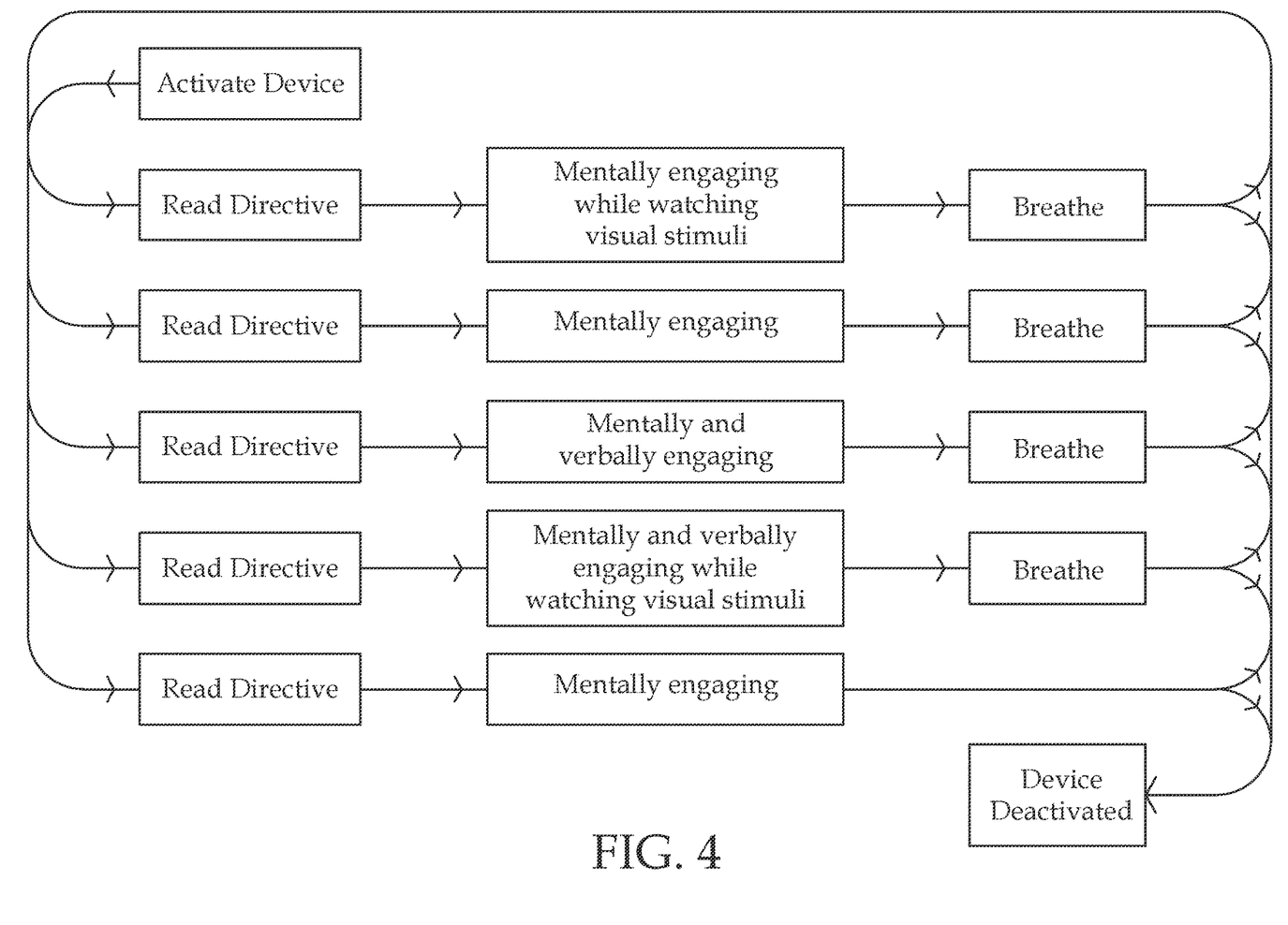
FIG. 4 depicts a flow chart showing a method for creating a list of directives for a particular individual.

FIG. 4 illustrates a preferably stationary individual 20 who is self-administering a session of brain programming. A brain programming self-administration system 100, hereinafter referred to as BPSAS, includes a list of directives 10. The list of directives 10 may be configured so that the individual 20 executing the list of directives 10 may self-administer a brain programming session. The list of directives may be configured to include directives that may require the individual to contemplate past, present and/or future events, emotions associated with those events, scenarios associated with those events, scenarios associated with those emotions, disposing of negative emotions, internalizing positive emotions, releasing negative emotions, and how an idealized version of the individual's self would interact with a scenario. As seen in FIG. 4, the list of directives 10 may be positioned so that the individual 20 can easily consult the list of directives 10 after executing a previous directive. However, in some embodiments, the list of directives 10 may be delivered to the individual 20 during a session via audio.

In the preferred embodiment, the BPSAS 100 includes an on/off switch 101, power cord 103, and further comprises a visual focus point 11 provided by a light source, and in the preferred embodiment an elongated LED bar 12 comprised of a plurality of LEDs in series. The visual focus point 11 is configured to be within a line of sight 5 of the individual while using the BPSAS 100 except for certain instances where the individual 20 may be reviewing the list of directives 10. The visual focus point 11 is configured to oscillate from one direction to another, ideally left to right as demonstrated by directional line 11*a*. The preferred elongated LED bar 12 is elongated along a horizontal plane, wherein the elongated LED bar 12 defines two longitudinal sides 13, 13' and two lateral sides 14, 14'. Upon reaching either lateral side 14, 14', the oscillating visual focus point 11 changes direction and travels toward the other lateral side 14', 14, repeating this process until the BPSAS 100 has run for thirty (30) seconds. The elongated LED bar 12 may be positioned within the line of sight 5 of the individual 20 so that the lateral sides 14, 14' are at predetermined opposite extremes of the individual's range of eye movement without moving their head from side to side. More particularly, the predetermined extremes are the right and left lateral extremes of the individual's lateral eye movement. Said visual focus point 11 is configured to provide visual stimuli to an individual self-administering a session of brain programming. In application, the individual 20 may enter a rapid eye movement (REM) sleep-like state while observing the oscillating visual focus point 11 which may contribute to the increase in synergy between pre- and post-session.

In one or more embodiments, the BPSAS 100 may include an audio stimulus device 15 for providing audio stimuli to the individual 20 and may include an audio knob 102 for volume control. The audio stimulus device 15 may be, but is not limited to, a wearable hearing device whether wired or wireless (such as but not limited to headphones and earbuds), a stereo, and a speaker or the like. In one or more embodiments, the audio device 15 may be configured to emit audio stimuli when the oscillating visual focus point 11 changes direction. In one or more embodiments, the audio device 15 may be configured to emit audio stimuli that is predominantly and/or exclusively detected by one ear of the individual when the oscillating visual focus point 11 reaches either lateral side 14, 14' and emit audio stimuli that is predominantly and/or exclusively detected by the other ear of the individual when the visual focus point 11 reaches the other lateral side 14, 14'. In the preferred embodiment, the BPSAS 100 may further include a haptic stimulus device 16 that is configured to provide haptic stimuli to the individual. The haptic stimulus device 16 is preferably a pair of handheld devices where one device is held by each hand of the individual, or a single handheld device held by both hands of the individual, but such a description should not be construed as limitation of the instant disclosure. The haptic device 16 may be configured to generate haptic stimuli when the oscillating visual focus point 11 changes direction. In one or more embodiments, the haptic device 16 may be configured to generate haptic stimuli that is predominantly and/or exclusively felt by one hand of the individual 20 whenever the visual focus point 11 reaches either lateral side 14, 14' and generate haptic stimuli that is predominantly and/or exclusively felt by the other hand of the individual 20 when the visual focus point 11 reaches the other lateral side 14', 14. Although not shown as would be understood the haptic device 16 may be wired or wireless and may include push buttons, joysticks, triggers or like for further control of the visual, audio, and haptic stimuli generated via BPSAS 100 such that the individual 20 could turn the visual focus point 11 or sound from audio device 15 on or off with the push of a button. As further understood the volume of the sound could also be controlled through haptic device 16 versus volume control knob 102. While not specified as further understood many variables could be associated with the stimuli of the device as well as controls for changing the same such as the tempo and brightness of the visual stimuli, the tone and volume of the audio, and the specific style of haptic stimuli generated such as vibrations, rumblings, and intensity of the same.

FIG. 3 shows an idealized representation of how a list of directives 10 may be created by someone skilled in the field of brain programming to be given to the individual 20 in advance of the individual's own self-administered session of brain programming. The list of directives 10 is preferably configured so that the individual 20 executes the list of directives 10 while experiencing the visual, haptic, and audio stimuli of the BPSAS 100. In one or more embodiments, the list of directives 10 may be configured to facilitate the individual 20 reducing their emotional response to a condition (i.e., anxiety, depression, inadequacy, worry, anger, etc.), to facilitate the individual 20 increasing positive emotions related to a recent experience or event, to facilitate the individual 20 reducing the emotional response to an event or similar events that have occurred in the past, to facilitate the individual 20 priming their mind for the state of success in the present to be prepared for a future event, and to facilitate the individual 20 priming their mind to be their future self. In one or more embodiments, the list of directives 10 may include directives such as, but not limited to: (a) activating the BPSAS 100; (b) mentally engaging with the content of a prompt, watching the visual focus point 11, and breathing; (c) mentally engaging with a prompt, and breathing; (d) mentally and verbally engaging with a prompt, and breathing; (e) mentally and verbally engaging with a prompt, watching the visual focus point 11, and breathing; (f) mentally engaging with a prompt; and (g) deactivating the BPSAS 100; and any combinations and permutations thereof.

As seen in FIG. 3, the present disclosure includes an embodiment of a method for individual administration of a brain programming session. The method comprising providing a device 100, preferably BPSAS 100 as described above. The method further comprises providing a list of directives 10 configured so that the individual 20 executing the list of directives 10 self-administers a brain programming session. A person skilled in the field of brain programming may prepare the list of directives 10 in advance of the individual's self-administered session. The method may further comprise positioning the visual focus point 11 within a line of sight 5 of the individual 20. The method preferably further comprises executing the list of directives 10 which may include the steps of activating the BPSAS 100 as a first directive and deactivating the BPSAS 100 as a final directive. In some embodiments, the BPSAS 100 may automatically deactivate after a period of time, for example, the time it would take to fully complete the list of directives 10. The list of directives 10 may include directives as listed above and below and in Examples 1-5 further described herein. The list of directives 10 is configured so that the individual 20 may execute the entire list in about ten minutes (+/–five minutes). Depending if the list of directives 10 is configured for reducing emotional responses to past events and conditions, breaking habits and making new habits, and/or for programming mind sets and emotions for future performances, after the individual 20 executes the method for individual administration of a brain programming session the individual 20 will have higher synergy when recalling past events and conditions or higher synergy when engaging in future performances or scenarios germane to the programmed mind set. As would be understood the directives are derived from the individual's initial brain programming based on their respective needs and may comprise any number of potential steps.

Figure 5:
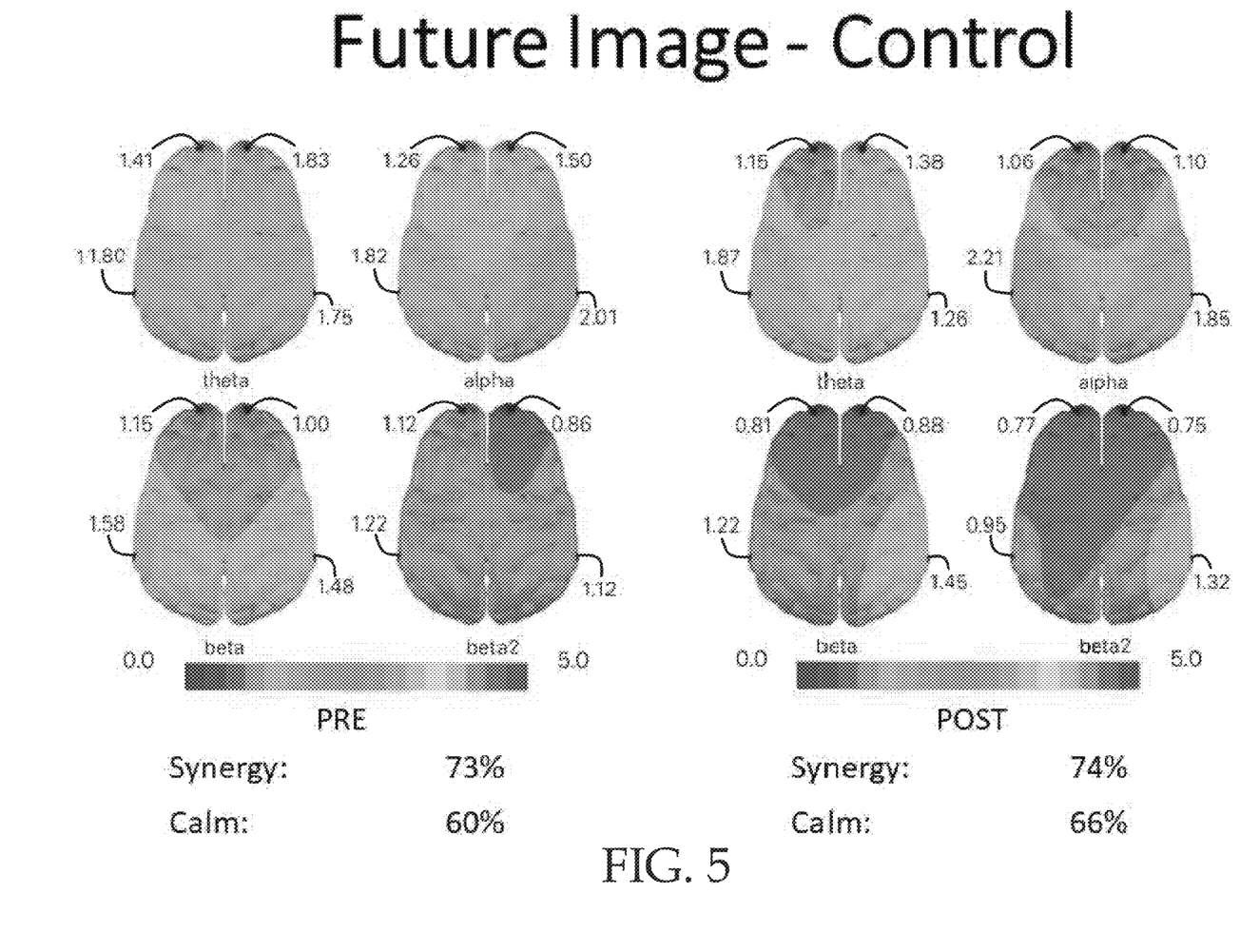
FIG. 5 shows before and after electrical activity diagrams of a Future Image-Control brain simply watching the lights, hearing the sounds, and feeling the vibration.
Figure 6:
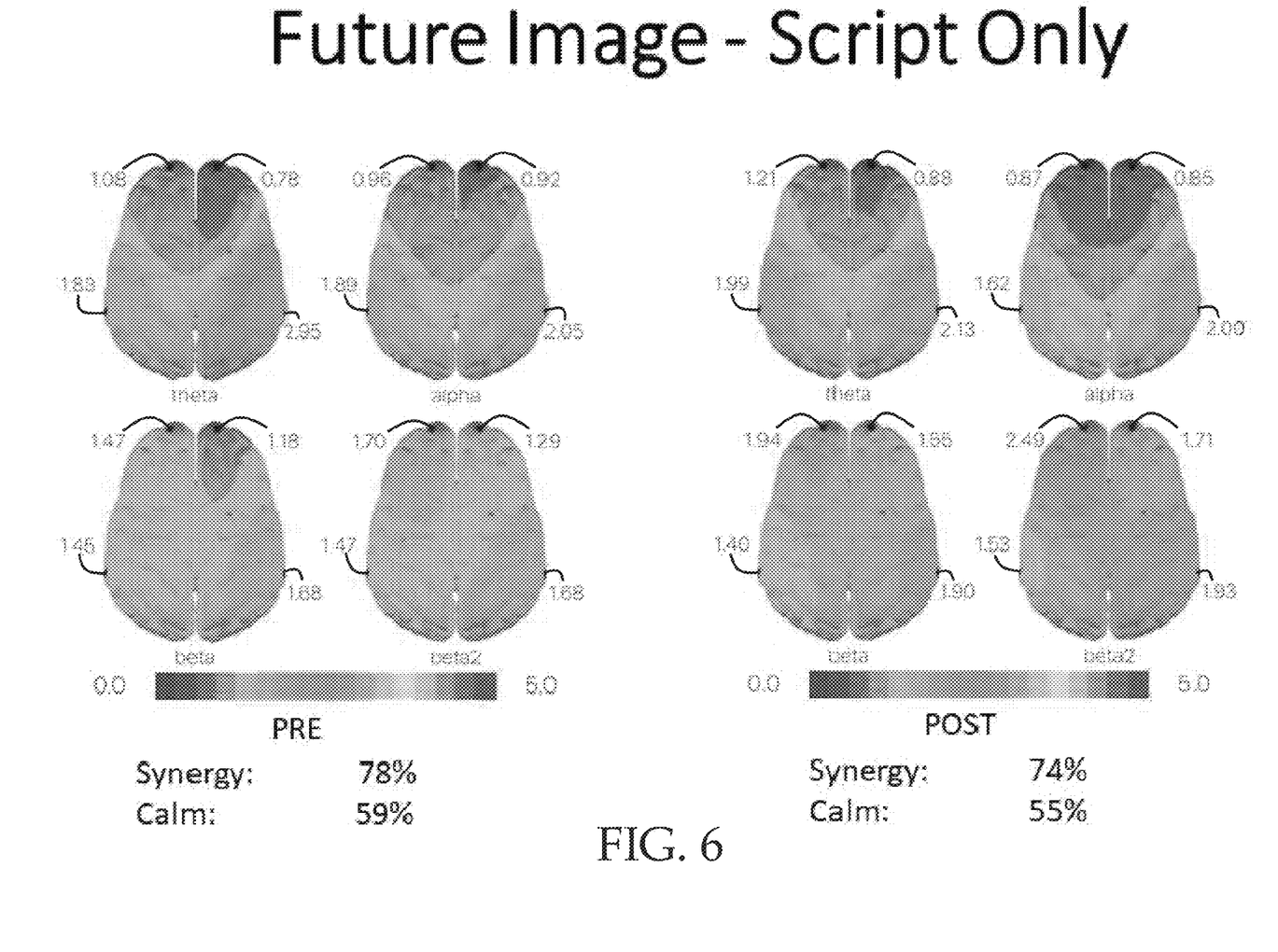
FIG. 6 illustrates before and after electrical activity diagrams of a brain exclusively engaging with only the Future Image-Script Only list of directives without the lights, sounds and vibrations.
Figure 7:
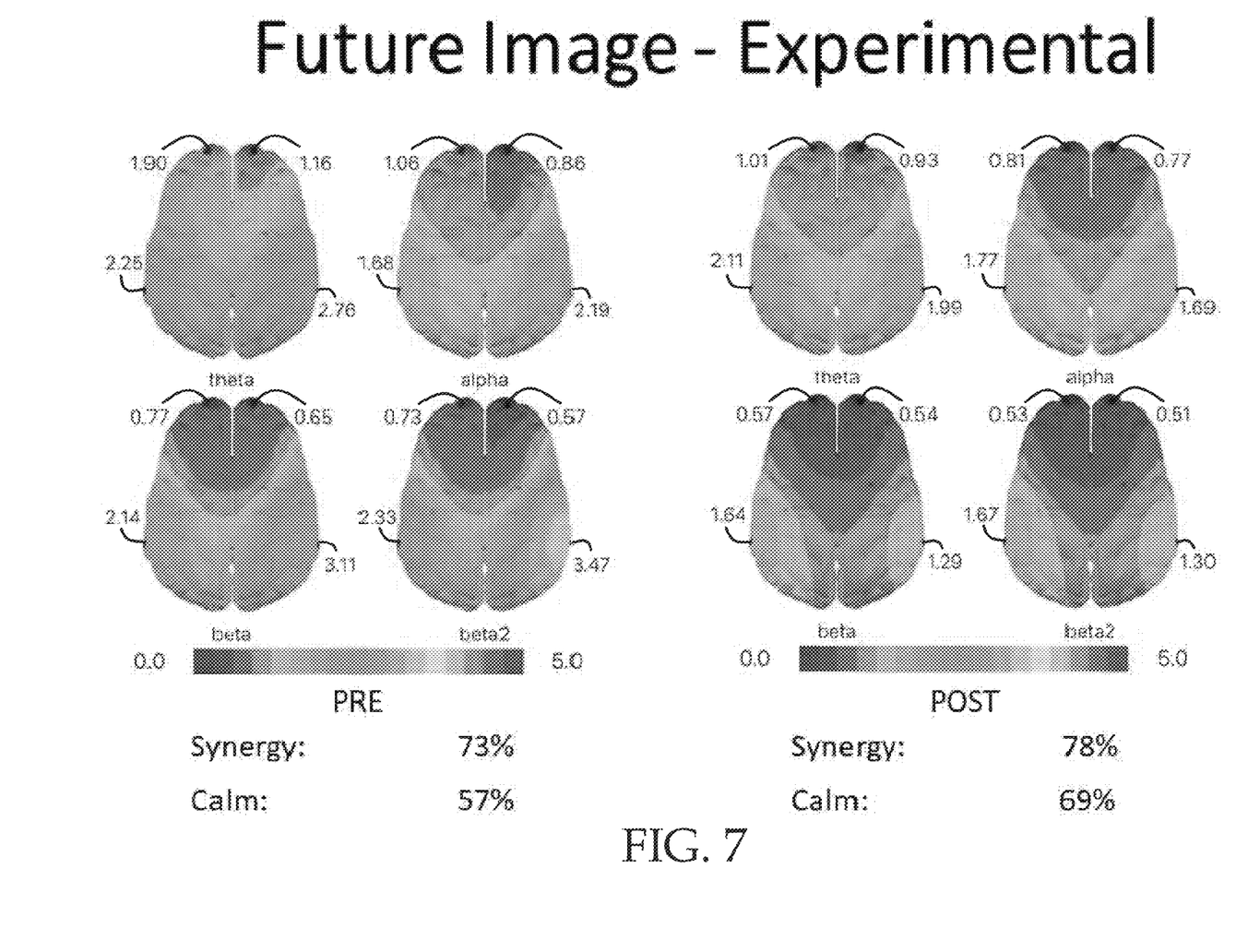
FIG. 7 illustrates before and after electrical activity diagrams of a brain engaging with the Future Image-Experimental list of directives and the individual programming self-administration system including lights, sounds and vibrations.

FIGS. 5, 6 and 7, illustrate testing completed to determine the effectiveness of the system and method for the brain programming self-administration. The four numerical values surrounding each brain represent the electrical activity of that region of the brain in microvolts and is measured where the black marks are positioned (near the front of the brain and rear sides of the brain). Note that the black marks near the rear of the brains are partially obscured by the image of the brain, but generally the measurement is taken near the rear set of numbers. The brains are also colored, depending on the coloring, a portion of the brain may be between zero microvolts at dark blue and five microvolts at red. Additionally, each of the four brains (pre- and post-) are measured at four different frequencies: theta (4 Hz-7 Hz), alpha (8 Hz-12 Hz), beta (13 Hz-20 Hz), and beta2 (21 Hz-30 Hz), generating sixteen total values for both the pre-set and post-set of brains. Generally, synergy is calculated by determining how coherent the sixteen values are to one another, the closer the sixteen values are to one another, the higher the synergy is. Coherence indicates how closely the signals are statistically related. FIGS. 5, 6, and 7 also show the calm value for the pre- and post-brains. Generally, calm is calculated by determining how low the sixteen values are, the lower values the greater value for calm.

The following reproduced excerpts are from the U.S. Pat. No. 8,990,054, titled System and Method for Determining and Training a Peak Performance State, which is incorporated in its entirety herein, and disclose how synergy may be calculated by determining the coherency of input signals.

Coherence in multiple signals can be identified substantially simultaneously and may involve conventional as well as unique systems and methods as a novel sequence of activity peaks and troughs.

Thereafter communicating input signals received from all of the sensors to the processor, analyzing the input signals by the processor with the algorithm as a function of their nonlinear relationship for determining coherency.

In the present disclosure, the preferred algorithm for coherency calculation is a combination of location and frequency band activity entered into an algorithm that determines the similarity of the brain pattern. In some other embodiments, the algorithm for coherency calculation is a combination of a manifold learning algorithm and a support vector machine algorithm.

Multiple measurements of physiological and non-physiological signals result in a high dimensional data set. One of ordinary skill in the art will understand that dimensionality of data for the purpose of this disclosure can mean the number of distinct non-overlapping values gathered from input signals. For example, movement of a limb can be captured by six elements (translation in three directions and rotations around three directions). These six measurements result in six dimensions. Similarly, an electroencephalogram (EEG) with fourteen channels has fourteen dimensions. Therefore, for an implementation of the present disclosure that includes both the EEG and movement of the limb, a total of twenty dimensions exists.

Modern data analysis tools are designed to work on high dimensional data whose components are not independently distributed. However, high dimensional spaces show surprisingly counter-intuitive geometrical properties that have a large influence on the performance of data analysis tools. This limits the application of traditional approaches to optimal physiological state detection. Direct linear or pairwise comparison of input signals to a peak performance standard is neither entirely accurate nor suitable for providing feedback when multiple dimensions are detected from input signals.

One approach to address high dimensional data is to reduce the dimensionality. There are many approaches to dimensionality reduction based on a variety of assumptions and used in several contexts. In some instances, high dimensional data may be simpler than the dimensionality would indicate. Specifically, a given high dimensional data set may contain many features that are all measurements of the same underlying cause and are therefore closely related. For example, the physiological state of "challenge" in human physiology is associated with elevated EEG and ECG signals in addition to a corresponding increase in skin temperature. This intuition may be formalized using the notion of a manifold: the data set lies along a low-dimensional manifold embedded in a high dimensional feature space. A nonlinear relationship may exist between low-dimensional manifold and high-dimensional feature representations. Manifold learning may provide the framework for analyzing nonlinear signal coherency. Therefore, use of a manifold learning algorithm is one embodiment of the present disclosure that efficiently projects high-dimensional data representing physiological and non-physiological input signals into low-dimensional data.

While a manifold may be obtained by linear techniques such as principal component analysis or linear discriminant analysis, these approaches are limited in high dimensionality situations both in terms of time and accuracy. As a nonlinear relationship may exist between a manifold and its high dimensional feature representation, it is preferable to obtain a manifold by nonlinear analysis techniques, for example the isomap approach, local linear embedding, laplacian eigenmaps, and semidefinite embedding. Algorithms for Manifold Learning by Lawrence Cayton (2005) gives a small representation of the algorithms that take high dimensional inputs and find their underlying manifold and is incorporated herein by reference.

Further, the manifolds in lower dimension space can be separated based on the expertise level or performance level of a test subject. For a given input signal being received, the algorithms for manifold learning project the high dimensional data point into lower dimensions. The closeness of the data point to manifolds for different classes reveals the identified class of the task as well as that of the test subject. The closeness can be defined by, for example, Euclidean distance, city block distance, or mahalanobis distance. It is this distance determination that is used as a comparison to the coherency of the multiple input signals.

FIG. 5 shows before and after images of a control brain exposed to no variables. As can be observed there is a negligible change in synergy from 73% to 74% between the before and after. Further, calm increases from 60% to 66%. FIG. 6 shows before and after images of a brain exposed to just the Future Image list of directives 10, a possible embodiment of this list of directives is shown below in Example 4. As can be seen, engaging with the Future Image list of directives 10 alone was shown to reduce synergy from 78% to 74%. Calm decreases from 59% to 55%. FIG. 7 shows before and after images of a brain engaging with the BPSAS 100 with a Future Image list of directives 10, where synergy levels rise from 73% to 78%. Calm increases from 57% to 69%. The combination of the BPSAS 100 with a Future Image list of directives 10 proves to be an effective method and system of increasing synergy and balance of a brain. This increase in synergy would facilitate the brain more easily making connections necessary to prepare for a future event or future state of being.

Figure 8:
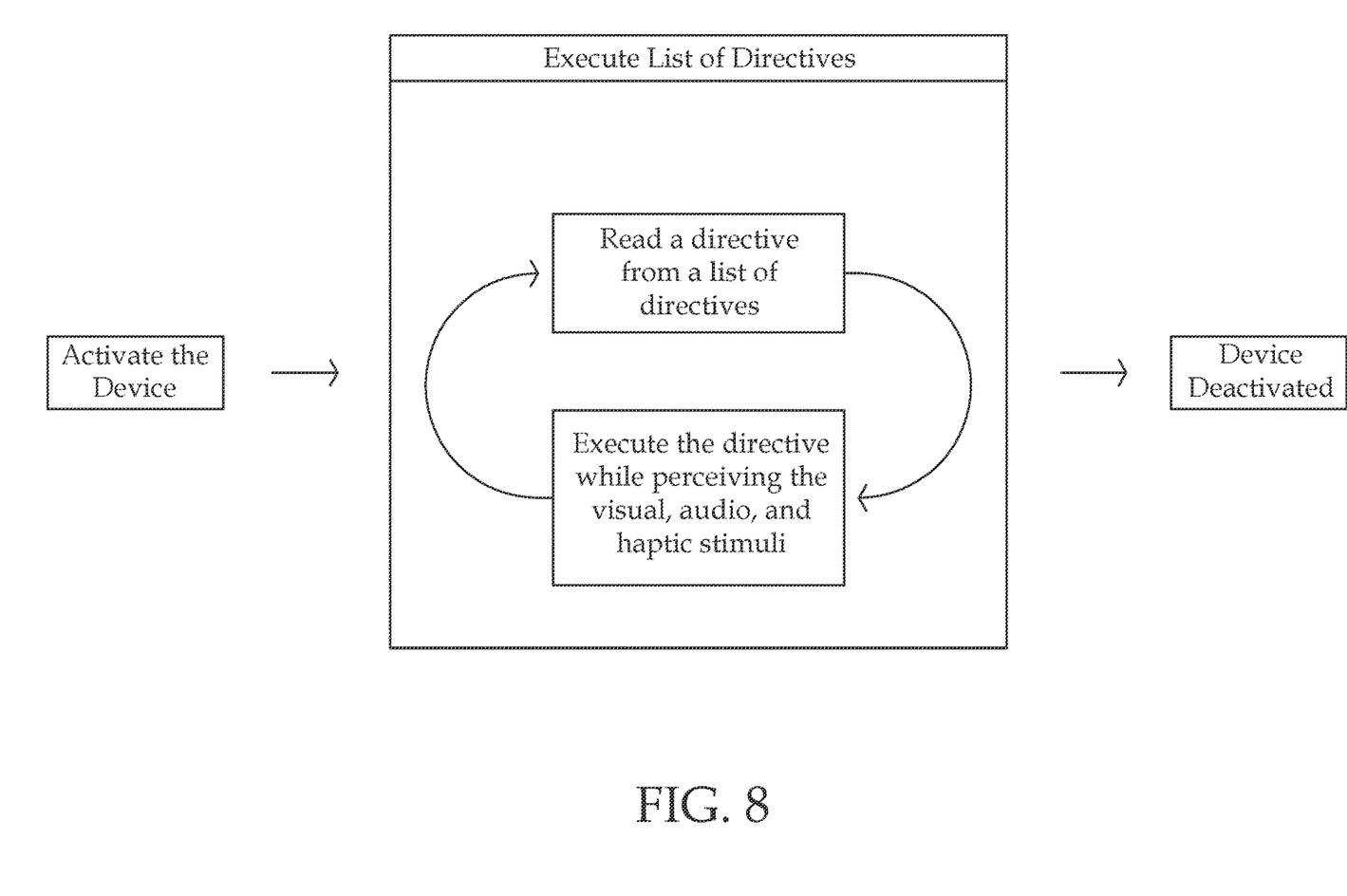
FIG. 8 shows a flow chart of the method for individual self-administration of brain programming.

As illustrated in FIG. 8, in the preferred embodiment, the individual 20 executes the list of directives 10 while experiencing the visual focus point 11, haptic stimuli from device 16, and audio stimuli from device 15, and depending on the content composition of the list of directives 10 as described above and seen in Examples 1-5 below, the individual 20 may reduce emotional response to past events and conditions and/or program mind sets and emotions for future performances and events. Completion or partial completion of the list of directives 10 while experiencing the visual focus point 11, haptic stimuli from device 16, and audio stimuli from device 15 may increase synergy and calm immediately after the brain programming session is concluded and may increase synergy and calm when recalling past events and conditions or engaging in future performances and future events.

After completing part of, or the entirety of, a list of directives 10 focused on reducing emotional response to past events and conditions, the individual 20 may have greater synergy when recalling the past events and conditions in the future. Ideally, the individual 20 will complete the same or similar list of directives 10 focused on reducing emotional response to past events and conditions multiple times so as to further increase the synergy when recalling the past events and conditions in the future compared to just executing the list of directives 10 one time or part of one time. Similarly, after completing part of, or the entirety of, a list of directives 10 focused on programming mind sets and emotional responses for future performances and events the individual's synergy may increase, and the individual 20 may have higher synergy than the individual 20 would otherwise have when encountering future performances and events. Ideally, the individual 20 will complete the same or similar list of directives 10 focused on programming mind sets and emotional responses for future performances and events multiple times so as to further increase the synergy when experiencing the performances and events in the future compared to just executing the list of directives 10 one time or part of one time. In some embodiments, the list of directives 10 may include a directive asking the individual 20 to create an idealized image of themselves and imagine scenarios in connection with this idealized image such has having the idealized image manage an event, having the idealized image experience an event, having the idealized image reflect how the individual perceives themselves, or having the idealized image experience a condition (such as but not limited to anxiety, inadequacy, expectations).

In some embodiments, the list of directives 10 may include directives asking the individual 20 to define a condition (such as but not limited to anxiety, inadequacy, expectations) or recall a past event; asking the individual 20 what feelings they feel when thinking about the condition or past event respectively; asking the individual to create an idealized image to interact with the feeling or past event respectively; asking the individual 20 to evaluate their feelings after the idealized image has interacted with the feeling or past event respectively; asking the individual 20 to create an event that could happen in the future and having the idealized image interact with the event; asking the individual 20 to evaluate their feelings while imagining this event; asking the individual 20 to verbally repeat a phrase out loud; asking the individual 20 to choose an idealized image and imagine what it is like to be that idealized image and imagine being closer to the individual's desires. After each directive, the individual 10 may be asked to take a breath. During certain directives, the individual 20 may be asked to watch the visual stimuli while engaging with the directive. During certain directives involving positive or negative emotions, the individual 20 may be directed to internalize positive emotions and release negative emotions.

In other embodiments, the list of directives 10 may include directives asking the individual 20 to relive a positive event or experience; asking the individual 20 to evaluate their feelings in connection with the positive event or experience, asking the individual 20 to create an idealized image of themselves to experience the same event or experience, asking the individual 20 to evaluate which characteristics present in the idealized image contributed to the positive feeling about the event or experience; asking the individual 20 to relive the event or experience again while focusing on the characteristics of the idealized image and the positive thoughts, feelings and behaviors during the event; asking the individual 20 to focus again on the positive feelings; asking the individual 20 to imagine another idealized image of their everyday self and internalizing the first idealized image; asking the individual 20 to evaluate their emotions, releasing negative emotions and internalizing positive emotions; and asking the individual 20 to verbally repeat a phrase out loud. After each directive, the individual 20 may be asked to take a breath. During certain directives, the individual 20 may be asked to watch the visual stimuli while engaging with the directive. During certain directives involving positive or negative emotions, the individual 20 may be directed to internalize positive emotions and release negative emotions.

In one or more embodiments, the list of directives 10 may include directives asking the individual 20 to imagine an upcoming event; asking the individual 20 to evaluate their feelings that arose while imagining the upcoming event; asking the individual 20 to consider which idealized image was engaging in this upcoming event; evaluating if there were any negative thoughts associated with the upcoming event and releasing them; asking the individual 20 to imagine an idealized image of who they want to be when engaging in this upcoming event and defining all the idealized images characteristics in detail; asking the individual 20 to internalize this new idealized image and the feelings of the idealized image; asking the individual 20 to evaluate whose perspective they are feeling the upcoming event from; asking the individual 20 to evaluate feelings and release the feelings if they are negative and internalize the feelings if they are positive; asking the individual 20 to verbally repeat a phrase out loud; and asking the individual 20 to choose a preferred idealized image for the future event and feel what it's like. After each directive, the individual 20 may be asked to take a breath. During certain directives, the individual 20 may be asked to watch the visual stimuli while engaging with the directive. During certain directives involving positive or negative emotions, the individual 20 may be directed to internalize positive emotions and release negative emotions.

Following are five examples of potential instructions and directives for use by the individual 20 in self-administering a session of brain programming using the brain programming self-administration system 100.

Example 1: Emotional Resilience Past Event

The following script is designed to assist you in reducing the emotional response to an event or similar events that have occurred in the past. Please follow each step of the guide as you watch, hear, and feel the lights, sound and vibration while remembering the event. You do not have to complete the whole event at once. You may want to do half and then rest, or a third and then rest, in order to complete the scenario. Please complete the guide at your own pace. Take a deep breath after stopping the lights each time.

1. Relive the event in your mind while watching the lights (push start and stop). You may review the event in sections if you choose. Breathe.
2. What feelings came up as you reviewed the event? Focus on releasing the feelings as you start and stop the light. Repeat if anything is left of the feelings. Breathe.
3. This time, step out of the event and watch that same experience as if you were watching it from outside yourself (start & stop the lights). Breathe.
4. Name and define the idealized image (authentic person you were being as you watched the event from this different perspective). What feelings came up watching it from the outside?
5. If the feelings are negative, use the lights to release them. Otherwise go to the next step.
6. If the feelings are positive, follow the lights and fill your body from the top of your head down to your toes with the positive feelings. Breathe.
7. Create a new authentic idealized image that is in charge. Name this idealized image. See yourself manage the event from above the way you would like to; watch the lights. Breathe.
8. What feelings were created while watching this event? If they are negative, use the lights to release them. If they were not negative, go to the next step. Breathe.
9. If these feelings are positive, use the lights to fill your body from the top of your head through the bottom of your feet. Breathe.
10. Create an event that could happen in the future. Choose the idealized image that you want to have manage this event. It can be the new one that you just named or create another new idealized image that you will now name (solution focused). See this idealized image manage the event as you watch the lights. Breathe.
11. What feelings came up while watching this event? If they are negative, release them with the lights. If they are not negative, go to the next step. Breathe.
12. If these feelings are positive, use the lights to fill your body from the top of your head down through the bottom of your feet. Breathe.
13. Please repeat this phrase as you watch the lights: "I totally love and accept all of my idealized image's. I can choose who I want to be at any moment in time." Breathe.
14. Lastly, see yourself choose any idealized image and feel what it is like being that person. Remember, you are all one (won) and anything you ever desire you can draw from above and shower yourself (outside and inside) from the top of your head to the bottom of your feet, as you watch the lights. Breathe.

Example 2: Emotional Resilience Condition

The following script is designed to assist you in reducing the emotional response to a condition (i.e., anxiety, not good enough, worry, anger, etc.). Please follow each step of the guide as you watch, hear, and feel the lights, sound and vibration while remembering the event. Please complete the guide at your own pace. Take a deep breath after stopping the lights each time.

1. Define the condition you would like to address (for example anxiety, not good enough, expectations, etc.). Imagine an idealized image experiencing this condition as you follow the lights. Name this idealized image (one character of your authentic self). Breathe.
2. What feelings came up while you watched this experience. Watch the lights and imagine releasing these negative feelings from your body. Breathe.
3. Now, create an image that represents the feeling. This will be an image that you can work with and change (i.e., 2-ton weight, dark clouds, imprisoned, etc.) as you watch the lights. Breathe.
4. Create an idealized image and a strategy that can be used to release the image you created (such as dropping a 2-ton weight or blowing the dark clouds away with a leaf blower, etc.) while viewing the lights. Repeat this step until the idealized image and the strategy have resolved the image (watch the lights). Breathe.
5. What feelings do you have after finding an idealized image and a strategy that works?
6. If the feelings are negative, release them from your body as you watch the lights. Otherwise go to the next step.
7. If these feelings are positive, imagine filling your body with that positive feeling from the top of your head to the bottom of your feet, while watching the lights. Breathe.
8. See yourself rise above the condition you would like to eliminate. You are no longer a part of the condition since it is below you. Let it be. It is no longer a part of you (while you watch the lights). Breathe.
9. Feel yourself above the condition without any need to engage with it in any way. Let it be as you watch the lights. Breathe.
10. Create an idealized image of the authentic character you would like to be in place of this condition idealized image (anxiety, not good enough, etc.). Imagine how the above "strategy" looks in a real-life solution(s) and watch the lights. Breathe.
11. Feel yourself being this new idealized image that you can call up from your authentic self at any time as you watch the lights. Breathe.
12. Create a future challenging situation as you watch the lights. Breathe.
13. Create and name an idealized image to be successful in this situation. It may be the same or different from your other idealized image's. Imagine being successful in the experience (follow the lights). Breathe.
14. What feelings came up while imagining this experience? If they are negative or doubtful, release them while watching the lights. Otherwise go to the next step. Breathe.
15. If these feelings are positive, fill your body from head to toe while watching the lights. Breathe.
16. Please repeat this phrase as you watch the lights: "I totally love and accept all of my idealized image's. I can choose who I want to be." Breathe.
17. Lastly, see yourself choose any idealized image and feel being that person as you watch the lights. Remember, you are all one (won) and anything you ever desire you can draw from above and shower yourself (outside and inside) from the top of your head to the bottom of your feet, as you watch the lights. Breathe.

Example 3: Emotional Priming Future Event

Bring your richly imagined future into the present. Close the gap between the future and now. Use neural programming to prime the mind for the state of success. The following script is designed to enhance the emotional mindset for an upcoming event(s). Please follow each step of the guide as you watch, hear and feel the lights, sound and vibration. You will be thinking and feeling the upcoming event. You do not have to complete the whole event at once. You may want to do half and then rest, or a third and then rest, in order to complete the scenario. Please complete the guide at your own pace. Take a deep breath after each time you stop the lights.

1. Put yourself in an upcoming event in your mind, while watching the lights (push start and stop). You may experience the event in sections if you choose. Breathe.
2. What feelings came up in your body as you imagined the event and watched the lights? Breathe.
3. What idealized image was engaging in this future event. If there were any negative or doubtful feelings as you engaged in the event, release them now as you start and stop the light. Repeat if anything is left of the negative or doubtful feelings. Breathe.
4. Who would you like to "Be" as you engage in this experience? Name this new idealized image (if different from the first idealized image) you are choosing to be and define all of their characteristics in detail as you watch the lights. Breathe.
5. Follow the lights and fill your body from the top of your head down to your toes with the feelings of the new idealized image (or first idealized image if they are the same) who will engage in this experience. Breathe.
6. Whose perspective do you feel at this future event? Is it more from the perspective of the old, idealized image or the new idealized image, or are they equal?
7. If there are any negative or doubtful feelings, please release them as you watch the lights. Otherwise go to the next step.
8. If these feelings are positive, use the lights to fill your body from the top of your head to the bottom of your feet. Breathe.
9. Please repeat this phrase as you watch the lights: "I totally love and accept myself. I can choose who I want to be at any moment in time." Breathe.
10. Lastly, see yourself choose your desired idealized image for this future event and feel being that person. Remember, you are all one (won) and anything you ever desire you can draw from above and shower yourself (outside and inside) from the top of your head to the bottom of your feet, as you watch the lights. Breathe.

Example 4: Emotional Priming Future Image

Bring your richly imagined future into the present. Close the gap between who you are now and who you aspire to be. Use neural programming to prime your mind and practice being this person. The following script is designed to enhance the emotional mindset for the successful person you choose to Be. Please follow each step of the guide as you watch, hear, and feel the lights, sound, and vibration. You will be thinking about this imagined person and all their characteristics. You do not have to complete the whole image at once. Please complete the guide at your own pace. Take a deep breath after each time you watch the lights.

1. Create the ideal image of who you aspire to be. Define this ideal person and all their characteristics in detail while watching the lights (push start and stop). You may create the image in sections if you choose. Breathe.

2. What feelings came up in your body as you imagined being this ideal person? If there were any negative or doubtful feelings, release them as you watch the lights? Repeat if anything is left of the negative or doubtful feelings. Otherwise go to the next step. Breathe.
3. If the feelings are positive, follow the lights and fill your body from the top of your head down to your toes with the feelings of this ideal you. Breathe.
4. Please repeat this phrase as you watch the lights: "I totally love and accept my ideal self." Breathe.
5. Now imagine a future event. Be your ideal self as you experience this event. Breathe.
6. What feelings came up in your body? If you have any negative or doubtful feelings, release them as you watch the lights. Repeat if any negative or doubtful feelings remain. Otherwise go to the next step. Breathe.
7. Once again, if they are positive, follow the lights and fill your body from the top of your head down to your toes with the feelings of this ideal you. Breathe.
8. Draw from above and shower yourself (outside and inside) from the top of your head to the bottom of your feet with love and light, as you watch the lights. Breathe.
9. If there is another future event you would like to imagine, please repeat steps 5 through 8. Breathe.
10. Imagine a past event that caused undesirable outcomes. Feel that idealized image. Breathe.
11. Invite your new ideal image to take over the event and change the outcome. Breathe.
12. Pull up an image of your younger self. The first one that comes to mind is good. See your younger self walking down a country road to meet your new ideal image. Breathe.
13. Please greet your younger self, however you choose. Listen to what they have to tell you. Breathe.
14. Respond to your younger self with responses you would like to share with them. Breathe.
15. Listen to them and continue the conversation until both of you are done. Say goodbye however you would like to part. Breathe.
16. Your new image of yourself is now closely connected to your younger self and the two of you will move forward, helping each other with any issues that arise. Check in with your younger self from time to time and know that you are always connected. Breathe.
17. What feelings came up for you when doing this? If they are negative, release them. Otherwise go to the next step. Breathe.
18. If these feelings are positive, follow the lights and fill your body from the top of your head down to your toes with the feelings of this ideal you. Breathe.
19. Draw from above and shower yourself (outside and inside) from the top of your head to the bottom of your feet with love and light, as you watch the lights. Breathe.

Example 5: Positive Past Experience/Event

The following script is designed to assist you in increasing positive emotions related to a recent experience/event. Please follow each step of the guide as you watch, hear and feel the lights, sound and vibration while remembering the event. You do not have to complete the event at once, you can break it up into smaller parts. Please complete the guide at your own pace. Take a deep breath after stopping the lights each time.

1. Relive the positive experience/event in your mind while watching the lights (push start). You may review the event in sections if you choose. Breathe.
2. What feelings are present as you relived the experience/event? Focus on the feelings and imagine the feelings fill your body from the top of your head to the bottom of your feet (as you watch the lights). Breathe.
3. Identify and name the idealized image that experienced this event. What characteristics were present in that idealized image that contributed to the positive feelings in the event (include positive self-talk and/or strategies used to be successful, is the idealized image confident, strong, etc.) as you watch the lights. Breathe.
4. Watch the event again and really focus on all aspects of this idealized image and the positive thoughts, feelings and behaviors during the event. Allow for all of the positive feelings to be present in your body (as you watch the lights). Breathe.
5. Focus on the positive feelings and once again, fill your body from the top of your head to the bottom of your feet with the feelings (as you watch the lights). Breathe.
6. Imagine your everyday idealized image, how do you see yourself. Then imagine that the idealized image you named and identified above merges with you. Watch the lights and let any feelings come up. Breathe.
7. If the feelings that came up were negative, watch the lights as you imagine releasing the negative feelings. Otherwise go to the next step. Breathe.
8. If the feelings are positive, watch the lights as you imagine filling yourself from the top of your head to the bottom of your feet with the feelings. Breathe.
9. Please repeat this phrase as you watch the lights: "I totally love and accept all of my idealized image's. I can choose who I want to be at any moment in time." Breathe.

As would be understood although this method and system is directed for self-administration, the user and/or trained professional would continue follow up to determine the strengths and/or weaknesses in the prescribed directives and the state of mind of the user after lengths of time, for example once a week, every other week, or once a month to determine if new or changed directives are needed. The path to retraining the mind to overcome traumatic events and/or associated stimuli is not to be taken lightly as each individual learns behaviors and comprehends understanding of their own unique triggers and the steps to move past them to a calmer, synergistic behavioral pattern.

The illustrations and examples provided herein are for explanatory purposes and are not intended to limit the scope of the appended claims.

We claim:
1. A method for individual administration of brain programming, the method comprising:
providing a device (100) configured to generate a visual focus point (11) that oscillates from one direction to another direction to provide visual stimuli, the device (100) further configured to provide haptic stimuli and audio stimuli;
providing a list of directives (10) configured so that an individual (20) executing the list of directives (10) self-administers a brain programming session;
positioning the visual focus point (11) within a line of sight (5) of the individual (20);
activating the device (100);
illuminating the visual focus point (11) defined by a light source;

oscillating the visual focus point (11) from one direction to another; executing the list of directives (10); and deactivating the device (100);

wherein the list of directives (10) includes asking an individual (20) at least one directive selected from the list comprising: to activate the device (100); to mentally engage with the content of a prompt, watch the visual focus point (11), and breathe; to mentally engage with a prompt, and breathe; to mentally and verbally engage with a prompt, and breathe; to mentally and verbally engage with a prompt, watch the visual focus point (11), and breathe; to mentally engage with a prompt; to deactivate the device (100); to define a condition or recall a past event; to define what feelings are felt when thinking about the condition or past event; to create an idealized image to interact with the feeling or past event; to evaluate the feelings felt after the idealized image has interacted with the feeling or past event; to create an event that could happen in the future and having the idealized image interact with the event; to evaluate the feelings felt while imagining this event; to verbally repeat a phrase out loud; to choose an idealized image and imagine what it is like to be that idealized image and imagine being closer to the desires of the individual; to relive a positive event or experience; to evaluate their feelings in connection with the positive event or experience, to create an idealized image of themselves to experience the same event or experience, to evaluate which characteristics present in the idealized image contributed to the positive feeling about the event or experience; to relive the event or experience again while focusing on the characteristics of the idealized image and the positive thoughts, feelings and behaviors during the event; to focus again on the positive feelings; to imagine another idealized image of their everyday self and internalizing the first idealized image; to evaluate their emotions, releasing negative emotions and internalizing positive emotions; to verbally repeat a phrase out loud; to imagine an upcoming event; to evaluate their feelings that arose while imagining the upcoming event; to consider which idealized image was engaging in this upcoming event; to evaluate if there were any negative thoughts associated with the upcoming event and releasing them; to imagine an idealized image of who the individual wants to be when engaging in this upcoming event and to define all the idealized images characteristics in detail; to internalize this new idealized image and the feelings of the idealized image; to evaluate whose perspective the individual is feeling the upcoming event from; to evaluate feelings and release the feelings if the feelings are negative and to internalize the feelings if the feelings are positive; to verbally repeat a phrase out loud; to choose a preferred idealized image for the future event and feel what it's like; to breathe between directives; to watch the visual focus point (11) while engaging with one or more directives; to internalize positive emotions and release negative emotions, and any combinations and permutations thereof.

2. The method for individual administration of brain programming of claim 1, wherein an elongated series of LEDs (12) generates the visual focus point (11).

3. The method for individual administration of brain programming of claim 1, wherein the oscillating of the visual focus point (11) occurs from left to right.

4. The method for individual administration of brain programming of claim 1, where the list of directives (10) includes instructing the individual (20) to perceive the visual focus point (11), audio stimuli, and haptic stimuli while executing the list of directives.

5. The method for individual administration of brain programming of claim 4, wherein the list of directives (10) includes one or more additional directives configured to reduce the individual's emotional response to a condition.

6. The method for individual administration of brain programming of claim 4, wherein the list of directives (10) includes one or more additional directives configured to prepare the individual (20) for a future event.

7. The method for individual administration of brain programming of claim 4, where the list of directives (10) includes one or more additional directives configured to reduce the individual's emotional response to a past event.

8. The method for individual administration of brain programming of claim 4, where the list of directives (10) includes one or more additional directives configured to facilitate the breaking of a habit of the individual (20) and the making of a new habit of the individual (20).

9. The system for individual administration of brain programming of claim 1, where the list of directives (10) includes instructing the individual (20) to perceive the visual focus point (11), audio stimuli, and haptic stimuli while executing the list of directives (10).

10. The system for individual administration of brain programming of claim 9, wherein the list of directives (10) includes one or more additional directives configured to reduce the individual's emotional response to a condition.

11. The system for individual administration of brain programming of claim 9, wherein the list of directives (10) includes one or more additional directives configured to prepare the individual (20) for a future event.

12. The system for individual administration of brain programming of claim 9, wherein the list of directives (10) includes one or more additional directives configured to reduce the individual's emotional response to a past event.

13. The system for individual administration of brain programming of claim 9, wherein the list of directives (10) includes one or more additional directives configured to facilitate the breaking of a habit of the individual (20) and the making of a new habit of the individual (20).

14. The system for individual administration of brain programming of claim 9, wherein the audio stimuli and the haptic stimuli are configured to activate whenever the visual focus point (11) changes direction from left to right and right to left.

15. The system for individual administration of brain programming of claim 14, wherein the audio stimuli and the haptic stimuli are configured to be exclusively perceived by a left ear and a left hand, respectively, of the individual (20) when the visual focus point (11) changes direction from left to right and to be exclusively perceived by the right ear and right hand, respectively, of the individual (20), when the visual focus point (11) changes direction from right to left.

16. A system for individual administration of a brain programming comprising:
- a list of directives (10), said list of directives (10) is configured so that an individual (20) executing the list of directives (10) self-administers a brain programming session;
- a device (100) configured to generate an oscillating visual focus point (11) defined by a light source, said oscillating visual focus point (11) moves from one direction to another direction (11a), said visual focus point (11) is positioned within a line of sight (5) of the individual (20), said device (100) is further configured to generate haptic stimuli (16) and audio stimuli (15); and wherein, the individual (20) executes the list of directives (10) while perceiving the visual focus point (11), the haptic stimuli, and the audio stimuli at predetermined times; and wherein the list of directives (10) includes asking an individual (20) at least one directive selected from the list comprising: to activate the device (100); to mentally engage with the content of a prompt, watch the visual focus point (11), and breathe; to mentally engage with a prompt, and breathe; to mentally and verbally engage with a prompt, and breathe; to mentally and verbally engage with a prompt, watch the visual focus point (11), and breathe; to mentally engage with a prompt; to deactivate the device (100); to define a condition or recall a past event; to define what feelings are felt when thinking about the condition or past event; to create an idealized image to interact with the feeling or past event; to evaluate the feelings felt after the idealized image has interacted with the feeling or past event; to create an event that could happen in the future and having the idealized image interact with the event; to evaluate the feelings felt while imagining this event; to verbally repeat a phrase out loud; to choose an idealized image and imagine what it is like to be that idealized image and imagine being closer to the desires of the individual; to relive a positive event or experience; to evaluate their feelings in connection with the positive event or experience, to create an idealized image of themselves to experience the same event or experience, to evaluate which characteristics present in the idealized image contributed to the positive feeling about the event or experience; to relive the event or experience again while focusing on the characteristics of the idealized image and the positive thoughts, feelings and behaviors during the event; to focus again on the positive feelings; to imagine another idealized image of their everyday self and internalizing the first idealized image; to evaluate their emotions, releasing negative emotions and internalizing positive emotions; to verbally repeat a phrase out loud; to imagine an upcoming event; to evaluate their feelings that arose while imagining the upcoming event; to consider which idealized image was engaging in this upcoming event; to evaluate if there were any negative thoughts associated with the upcoming event and releasing them; to imagine an idealized image of who the individual wants to be when engaging in this upcoming event and to define all the idealized images characteristics in detail; to internalize this new idealized image and the feelings of the idealized image; to evaluate whose perspective the individual is feeling the upcoming event from; to evaluate feelings and release the feelings if the feelings are negative and to internalize the feelings if the feelings are positive; to verbally repeat a phrase out loud; to choose a preferred idealized image for the future event and feel what it's like; to breathe between directives; to watch the visual focus point (11) while engaging with one or more directives; to internalize positive emotions and release negative emotions, and any combinations and permutations thereof.

17. The system for individual administration of brain programming of claim 16, wherein an elongated series of LEDs (12) generates the visual focus point (11).

18. The system for individual administration of brain programming of claim 16, wherein the visual focus point (11) oscillates from left to right.

* * * * *